United States Patent [19]

Milish

[11] Patent Number: 4,537,219
[45] Date of Patent: Aug. 27, 1985

[54] FLUID-SAMPLING VALVE FOR A HYDRAULIC SYSTEM

[75] Inventor: William P. Milish, Bristol, Conn.

[73] Assignee: Transamerica DeLaval, Inc., Princeton, N.J.

[21] Appl. No.: 539,797

[22] Filed: Oct. 7, 1983

[51] Int. Cl.³ .............................................. F16K 17/168
[52] U.S. Cl. ................................ 137/614.19; 137/504; 222/397; 251/120
[58] Field of Search ............... 137/504, 614.19, 878, 137/879, 881, 883; 251/120; 222/80, 82, 396, 397

[56] References Cited

U.S. PATENT DOCUMENTS

| | | | |
|---|---|---|---|
| Re. 23,487 | 4/1952 | McCabe, Jr. | 137/614 X |
| 1,860,046 | 5/1932 | McCutcheon | 137/614.19 X |
| 2,388,026 | 10/1945 | Ward | 222/396 X |
| 2,548,352 | 4/1951 | Courtot | 137/881 X |
| 2,877,796 | 3/1959 | Abdo | 137/594 X |
| 3,015,341 | 1/1962 | Hedland et al. | 137/504 X |
| 3,319,648 | 5/1967 | Donner | 137/504 |
| 3,319,717 | 5/1967 | Chenoweth | 137/504 X |
| 3,502,111 | 3/1970 | Hansen | 251/120 X |
| 3,863,673 | 2/1975 | Sitton | 251/120 X |
| 4,078,578 | 3/1978 | Buchholz | 137/614.19 X |

Primary Examiner—A. Michael Chambers
Assistant Examiner—John C. Fox
Attorney, Agent, or Firm—Hopgood, Calimafde, Kalil, Blaustein & Judlowe

[57] ABSTRACT

For the purpose of safely sampling fluid from a high pressure hydraulic system there is provided a valve assembly in which the passage of fluid through a fluid flow passage in a valve housing is controlled by a pressure regulated flow velocity limiting valve followed by an external lever controlled passage occluding poppet valve. The flow passage feeds a needle nosed nozzle with all passages sized to limit the discharge flow velocity to a safe maximum. A pressure relief valve is provided to divert fluid to a safe discharge if nozzle flow should become impeded and pressure should build up above a predetermined level.

17 Claims, 7 Drawing Figures

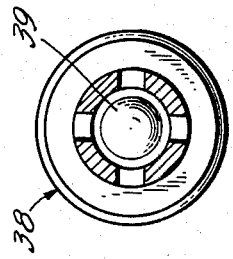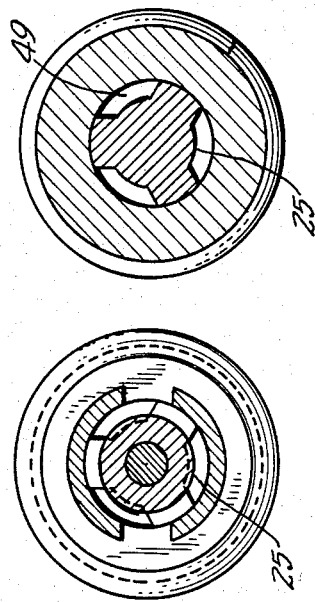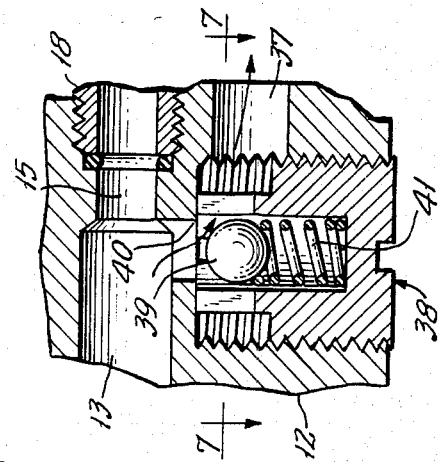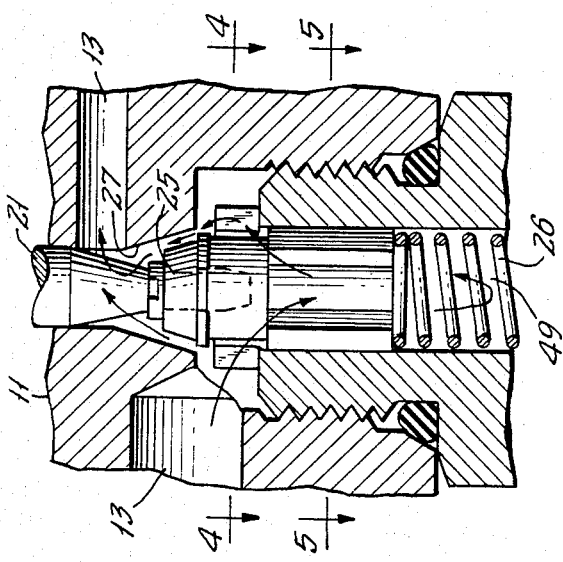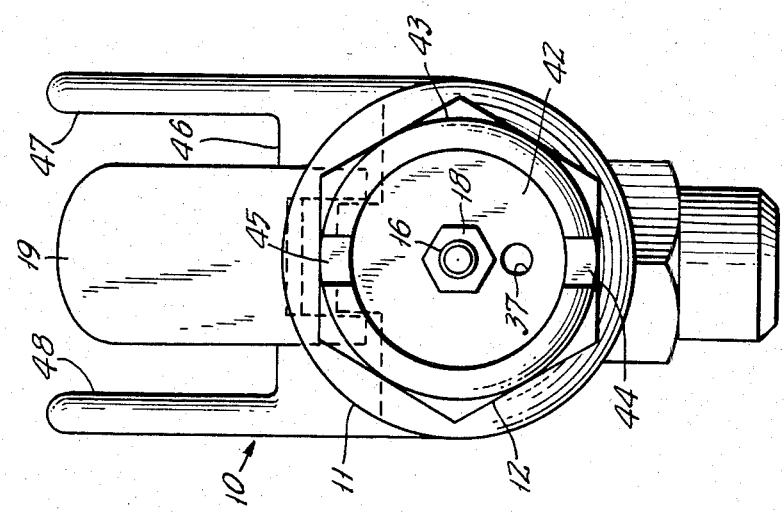

FLUID-SAMPLING VALVE FOR A HYDRAULIC SYSTEM

BACKGROUND OF THE INVENTION

The present invention relates to valve assemblies and, more particularly, to a valve assembly for use in sampling fluids.

High pressure hydraulic systems experience failures as a result of abrasion and wear of critical component parts either due to the natural abrasion of high pressure high velocity fluid flow acting directly on the components or due to inter-component abrasion where moving parts operate in a high pressure environment. In either case, certain types of failure can be costly or even catastrophic if they are not detected in the incipient stage and no remedial action is taken. One method of detecting incipient failure is to obtain a sample of the hydraulic fluid from the operating system and analyze such sample for the presence of contaminants. For example, a pump in the system may be experiencing wear or erosion and metal from its parts is entering the fluid stream. Detection of such metal in the fluid sample would provide an indication and warning of the potential risk factor.

Apparatus is known for monitoring the fluid in hydraulic systems where the pressure can reach as high as 6000 p.s.i.g. or higher. Such apparatus makes use of a check-valve-controlled tap installed in the hydraulic system to which valve can be connected, by means of a suitable female coupling, a length of small bore flexible hose. The coupling for attaching the hose to the check-valve-controlled tap has a coaxial nipple that penetrates the check valve to unseat the latter upon tightening the female threaded coupling. Generally, a pressure gauge is connected to the free end of the hose and the arrangement is used for briefly observing the pressure at the site of the tap.

If the high pressure check-valve-controlled tap mentioned above is to be used for extracting fluid samples for testing, it is extremely difficult and dangerous to rely upon manipulation of the check valve through the intermediary of the hose coupling for controlling the flow of sampled fluid. It is, therefore, an object of the present invention to provide a valve assembly that can be used safely for extracting a controlled quantity of the hydraulic fluid under conditions that will not introduce additional contamination.

SUMMARY OF THE INVENTION

In accordance with the present invention there is provided a valve assembly for use in sampling fluids from high pressure hydraulic systems, said assembly comprising in combination a housing, a fluid flow passage through said housing from an inlet port to an outlet port, a nozzle coupled to said outlet port, means for selectably starting and stopping the flow of fluid through said flow passage, means for limiting the flow velocity of said flow of fluid substantially independent of input fluid pressure, and means for diverting fluid from said outlet port to a vent port if fluid pressure at said outlet port exceeds a predetermined level.

BRIEF DESCRIPTION OF THE DRAWINGS

The invention will be better understood after reading the following detailed description of the presently preferred embodiment thereof with reference to the appended drawings in which:

FIG. 2 is a elevational end view of the nozzle end of the valve of FIG. 1;

FIG. 3 is a fragmentary view to an enlarged scale of the flow starting and stopping means of the valve of FIG. 1 showing the parts in the valve open position;

FIG. 4 is a transverse sectional view taken along the line 4—4 in FIG. 3;

FIG. 5 is a transverse sectional view taken along the line 5—5 in FIG. 3;

FIG. 6 is a fragmentary view to an enlarged scale of the flow diverting means (the pressure relief valve) of the valve of FIG. 1 showing the diverting means in flow passing position; and FIG. 7 is a transverse sectional view taken along the line 7—7 in FIG. 6.

The same reference numerals are used throughout the drawings to designate the same or similar parts.

DETAILED DESCRIPTION OF THE PRESENTLY PREFERRED EMBODIMENT

Figure 1:
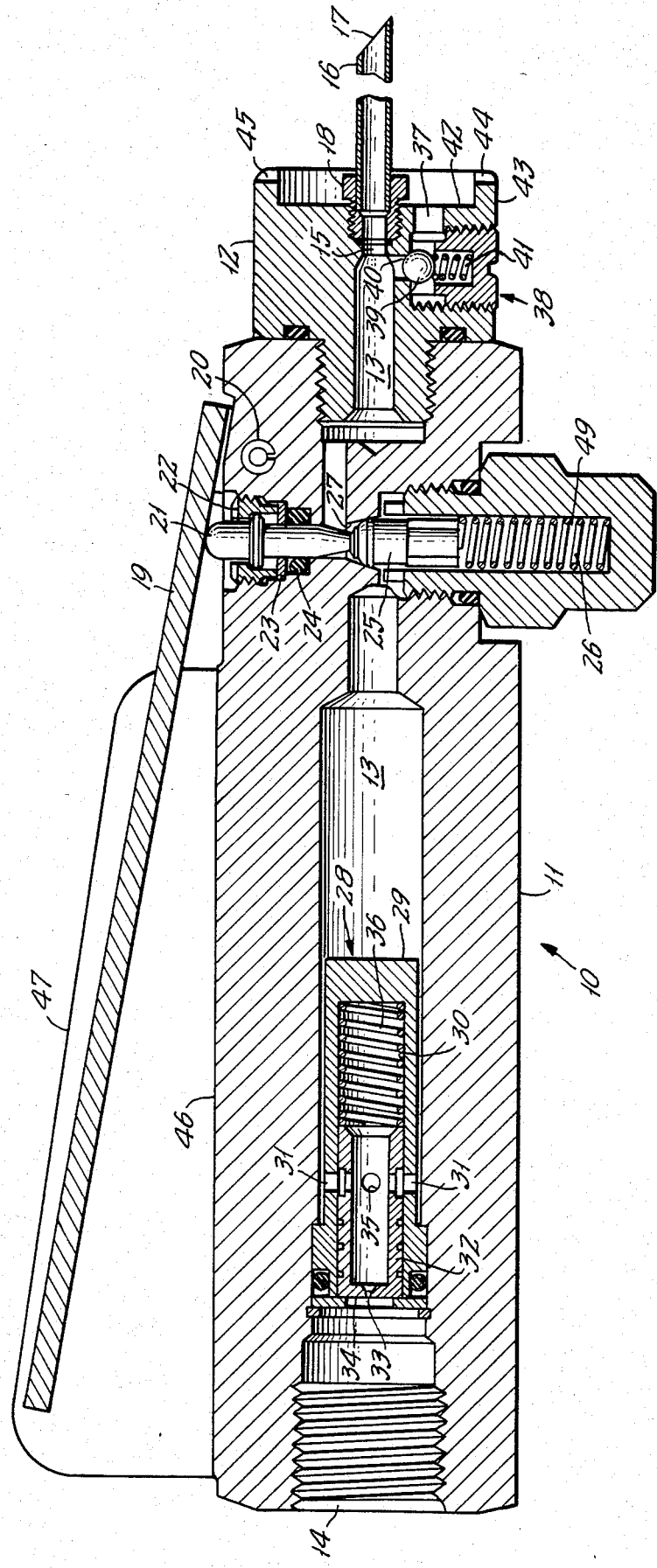
FIG. 1 is a longitudinal sectional view through a valve assembly embodying the present invention, the parts being shown in valve closed position.

Sampling of hydraulic fluid is accomplished by introducing a quantity of the fluid into a sampling bottle or similar container. A typical sample may range between about 8 and 16 fluid ounces although the quantity is not critical nor a part of the present invention. The bottle is maintained in a sterile condition using techniques conventionally employed in biological sampling and is closed by a self-sealing diaphragm that can be penetrated by a small diameter tube, resembling a hypodermic needle but substantially larger in size, which diaphragm reseals itself upon withdrawal of the tube.

Referring to the drawings, the new valve assembly is shown as comprising a housing 10 having a main body portion 11 and a cap portion 12. A fluid flow passage 13 extends generally longitudinally through the housing 10 from an inlet port 14 in the main body portion 11 to an outlet port 15 in the cap portion 12. A nozzle 16 in the form of a small bore tube with a needle nose 17 at one end is coupled by a threaded coupling member 18 to the outlet port 15. A manually operable lever 19, pivotally joined at 20 to the body portion 11, bears upon an actuator member or pin 21 guided within an insert 22 that also serves to retain a washer 23 and O-ring seal 24 around the pin 21. The actuator pin 21 bears against a poppet valve 25 biased by a compression spring 26 into fluid sealing engagement with a valve seat 27. The seat 27 is disposed, as shown, within the flow passage 13.

One important feature of the subject valve assembly is the inclusion of means for limiting the flow velocity of the fluid passing through the flow passage 13 irrespective of any variation in input fluid pressure. Such limiting means takes the form of a spring biased regulator valve 28. The valve 28 comprises a body 29 disposed in the flow passage 13 near the inlet port 14. The body 29 has a cylindrical axial counterbore 30 with side-wall ports 31, e.g., six in number uniformly distributed circumferentially. A valve spool 32 is disposed in the counterbore 30 with a sliding fit and has a restricted orifice 33 in a pressure head 34 at its outer end and lateral apertures 35 in its side wall. There is also provided within the counterbore 30 a biasing spring 36 for resisting inward movement of the valve spool 32.

The regulator valve 28 functions to restrict the fluid flow rate and is related to the dimensions of the passage 13 through the housing 10 so as to limit the flow velocity. While from a consideration of safety one might consider reducing the flow velocity without limit, too low a velocity gives rise to a problem. The purpose of the sampling valve is to extract fluid so as to test for contaminants. However, if the velocity is too low the valve will behave as a filter permitting entrained particles to precipitate or settle out of the fluid, particularly where there are abrupt changes in direction within the fluid passages. As a consequence, while it does not represent a critical lower limit, it is presently contemplated to size the orifice 33 in regulator valve 28 relative to all the other parameters to limit the flow rate to about 0.18 GPM. The dimensions of passage 13 are such that the maximum internal flow velocity for such flow rate is about 72 ft./sec. At the outlet tube or nozzle 16 the corresponding maximum flow velocity is about 7.2 ft./sec., a fluid velocity that is well within the limits of that which is safe to handle and which cannot injure a human operator. Anything below about 10 to 15 ft./sec. should be safe.

Although the flow rate and velocity is limited, it is still possible for a dangerous condition to develop if for some reason flow through the nozzle 16 should become impeded and pressure should build up in the vicinity of the outlet port 15. To insure against this possibility there is provided means for diverting fluid from the outlet port 15 to a vent port 37 if fluid pressure at outlet port 15 exceeds a predetermined safe level. The diverting means comprises a spring biased pressure relief valve 38 having a ball valve 39 cooperating with a valve seal 40 and regulated by a compression spring 41. It is presently preferred to arrange for relief valve 38 to open at 30 p.s.i.g. and to thereupon pass fluid to the vent port 37 which opens into a cavity 42 formed within the end of the housing 10 and, more specifically, in the end of the cap portion 12. The cavity 42 surrounds the outlet port 15 and is bounded by a skirt 43 extending in the direction of the nozzle 16. Openings 44 and 45 are provided in the skirt 43 for the discharge of fluid passed by the relief valve 38 when the housing 10 is pressed against a membrane that engages the skirt 43. Any discharge through openings 44 and 45 will be essentially harmless.

As best seen in FIG. 2, the actuating lever 19 is located in a channel 46 between guard flanges 47 and 48 to reduce the risk of undesired or accidental manipulation of the lever.

The flow regulator provides an adjustable orifice that closes as fluid pressure at inlet port 14 increases. The adjustable orifice is provided by the variable area overlap between the apertures 35 in the valve spool 32 and the side-wall ports 31 in the valve body 29. This arrangement regulates the flow rate in known manner.

In the valve closed position shown in FIG. 1, fluid under full line pressure fills the chamber 49 behind the poppet valve 25 aiding spring 26 in maintaining the valve-closed condition. However, due to the flow restriction provided by regulator valve 28, the pressure will fall sharply when poppet valve 25 is opened by depressing lever 19. Fluid then flows up, as seen in FIG. 3, past the valve seat 27 and then to the outlet port 15 and nozzle 16. Assuming no blockage, the fluid will discharge through nozzle 16.

Upon releasing lever 19, it will be apparent that fluid has access to both sides of the poppet valve and therefore exerts little force thereon. The dynamic fluid forces will be directed in the valve closing direction and will aid spring 26 in closing poppet valve 25 against its seat 27. This provides for extremely rapid valve response.

If, while poppet valve 25 is unseated, nozzle 16 should become blocked, excessive fluid pressure will be vented through relief valve 38. Such venting will be controlled and directed to avoid injury to the valve operator.

Having described the presently preferred embodiment of the invention it should be apparent to those skilled in the subject art that various changes in construction can be introduced without departing from the true spirit of the invention as defined in the appended claims.

What is claimed is:

1. A valve assembly for use in sampling fluids from high pressure hydraulic systems, said assembly comprising in combination a housing, a fluid flow passage through said housing from an inlet port to an outlet port, a nozzle coupled to said outlet port, means for selectably starting and stopping the flow of fluid through said flow passage, means for limiting the flow velocity of said flow of fluid substantially independent of input fluid pressure, and means including positive-pressure-responsive valve means for diverting fluid from said outlet port to a vent port if fluid pressure at said outlet port exceeds ambient pressure by a predetermined amount.

2. A valve assembly according to claim 1, characterized in that said positive-pressure-responsive valve means comprises a spring biased pressure relief valve.

3. A valve assembly according to claim 2, characterized in that said flow velocity limiting means comprises a spring biased regulator valve.

4. A valve assembly according to claim 3, characterized in that said regulator valve comprises a body disposed in said flow passage near the inlet port, said body having a cylindrical axial counterbore with side-wall ports, a valve spool disposed in said counterbore with a sliding fit and having a restricted orifice in a pressure head at its outer end and lateral apertures in its side wall, and a biasing spring within said counterbore for resisting inward movement of said valve spool.

5. A valve assembly according to claim 4, characterized in that said vent port opens into a cavity formed within the end of said housing surrounding said outlet port, said cavity being bounded by a skirt extending in the direction of said nozzle, and openings in said skirt for the discharge of fluid passed by said relief valve when said housing is pressed against a membrane which would otherwise seal off said cavity.

6. A valve assembly according to claim 2, characterized in that said vent port opens into a cavity formed within the end of said housing surrounding said outlet port, said cavity being bounded by a skirt extending in the direction of said nozzle, and openings in said skirt for the discharge of fluid passed by said relief valve when said housing is pressed against a membrane which would otherwise seal off said cavity.

7. A valve assembly according to claim 6, characterized in that said nozzle has a membrane piercing tip for introduction through a membrane into a sampling container, and said skirt is arranged to engage such membrane upon insertion of said nozzle to confine and control any overpressure fluid discharge past said relief valve.

8. A valve assembly according to claim 1, characterized in that said flow velocity limiting means comprises a spring biased regulator valve having a body disposed in said flow passage near the inlet port, said body having a cylindrical axial counterbore with side-wall ports, a valve spool disposed in said counterbore with a sliding fit and having a restricted orifice in a pressure head at its outer end and lateral apertures in its side wall, and a biasing spring within said counterbore for resisting inward movement of said valve spool.

9. A valve assembly according to claim 1, characterized in that said means for selectably starting and stopping said flow comprises a valve seat in said flow passage, a spring biased poppet valve disposed for movement in said housing into and out of flow occluding relationship with said valve seat, and a manually manipulable actuator member for unseating said poppet valve.

10. A valve assembly according to claim 9, characterized in that said flow velocity limiting means comprises a spring biased regulator valve having a body disposed in said flow passage near the inlet port, said body having a cylindrical axial counterbore with side-wall ports, a valve spool disposed in said counterbore with a sliding fit and having a restricted orifice in a pressure head at its outer end and lateral apertures in its side wall, and a biasing spring within said counterbore for resisting inward movement of said valve spool.

11. A valve assembly according to claim 9, characterized in that said positive-pressure-responsive valve means comprises a spring biased pressure relief valve.

12. A valve assembly according to claim 11, characterized in that said flow velocity limiting means comprises a spring biased regulator valve having a body disposed in said flow passage near the inlet port, said body having cylindrical axial counterbore with side-wall ports, a valve spool disposed in said counterbore with a sliding fit and having a restricted orifice in a pressure head at its outer end and lateral apertures in its side wall, and a biasing spring within said counterbore for resisting inward movement of said valve spool.

13. A valve assembly according to claim 12, characterized in that said vent port opens into a cavity formed within the end of said housing surrounding said outlet port, said cavity being bounded by a skirt extending in the direction of said nozzle, and openings in said skirt for the discharge of fluid passed by said relief valve when said housing is pressed against a membrane which would otherwise seal off said cavity.

14. A valve assembly according to claim 13, characterized in that said nozzle has a membrane piercing tip for introduction through a membrane into a sampling container, and said skirt is arranged to engage such membrane upon insertion of said nozzle to confine and control any overpressure fluid discharge past said relief valve.

15. A valve assembly according to claim 7, characterized in that said vent port opens into a cavity formed within the end of said housing surrounding said outlet port, said cavity being bounded by a skirt extending in the direction of said nozzle, and openings in said skirt for the discharge of fluid passed by said diverting means when said housing is pressed against a membrane which would otherwise seal off said cavity.

16. A valve assembly for use in sampling fluids from high pressure hydraulic systems, said assembly comprising in combination a housing, a fluid flow passage through said housing from an inlet port to an outlet port, a nozzle coupled to said outlet port, means for selectably starting and stopping the flow of fluid through said flow passage, means for limiting the flow velocity of said flow of fluid substantially independent of input fluid pressure, means including positive-pressure-responsive valve means for diverting fluid from said outlet port to a vent port if fluid pressure at said outlet port exceeds ambient pressure by a predetermined amount, said vent port opening into a cavity formed within the end of said housing surrounding said outlet port, said cavity being bounded by a skirt extending in the direction of said nozzle, and openings in said skirt for the discharge of fluid passed by said relief valve when said housing is pressed against a membrane which would otherwise seal off said cavity.

17. A valve assembly according to claim 16, characterized in that said nozzle has a membrane piercing tip for introduction through a membrane into a sampling container, and said skirt is arranged to engage such membrane upon insertion of said nozzle to confine and control any overpressure fluid discharge past said diverting means.

* * * * *

UNITED STATES PATENT AND TRADEMARK OFFICE
CERTIFICATE OF CORRECTION

PATENT NO. : 4,537,219

DATED : August 27, 1985

INVENTOR(S) : William P. Milish

It is certified that error appears in the above-identified patent and that said Letters Patent are hereby corrected as shown below:

Column 6, line 10, "claim 7" should read --claim 9--.

Signed and Sealed this

Seventh Day of October, 1986

[SEAL]

*Attest:*

DONALD J. QUIGG

*Attesting Officer*   *Commissioner of Patents and Trademarks*